US009322746B2

(12) United States Patent
Mihaylov et al.

(10) Patent No.: US 9,322,746 B2
(45) Date of Patent: Apr. 26, 2016

(54) SAMPLING BAG WITH MULTILAYER WALLS

(71) Applicant: Nextteq LLC, Tampa, FL (US)

(72) Inventors: Gueorgui M. Mihaylov, Virginia Beach, VA (US); Bryan I. Truex, Tampa, FL (US)

(73) Assignee: NEXTTEQ LLC, Tampa, FL (US)

( * ) Notice: Subject to any disclaimer, the term of this patent is extended or adjusted under 35 U.S.C. 154(b) by 357 days.

(21) Appl. No.: 13/729,590

(22) Filed: Dec. 28, 2012

(65) Prior Publication Data

US 2013/0180345 A1    Jul. 18, 2013

Related U.S. Application Data

(60) Provisional application No. 61/580,863, filed on Dec. 28, 2011.

(51) Int. Cl.
*G01N 1/12* (2006.01)
*G01N 1/00* (2006.01)
(Continued)

(52) U.S. Cl.
CPC .. *G01N 1/00* (2013.01); *G01N 1/10* (2013.01); *G01N 1/22* (2013.01)

(58) Field of Classification Search
CPC .................................. B65D 33/00; G01N 1/12
USPC ............................ 73/863.23, 864.83, 864.51, 73/864.62–864.64, 864.91; 383/107, 108, 383/109, 116, 3, 104, 119–121, 105; 380/88–92, 105, 109, 104, 114, 380/119–121
See application file for complete search history.

(56) References Cited

U.S. PATENT DOCUMENTS 3,266,710 A * 8/1966 Reeves .................... B31B 37/00
156/203
3,394,871 A * 7/1968 Williams ............... B65D 31/00
383/100

(Continued)

FOREIGN PATENT DOCUMENTS

EP        0905570      12/2002
EP        1045656       1/2003

(Continued)

OTHER PUBLICATIONS

Supplementary European Search Report for Application No./Patent No. 12861589.5-1553 / 2798330 PCT/US2012072002, dated Jul. 15, 2015.

*Primary Examiner* — Hezron E Williams
*Assistant Examiner* — Hoang Nguyen
(74) *Attorney, Agent, or Firm* — Pike IP Law, PLLC; Bernard G. Pike

(57) ABSTRACT

Sample bags having at least one multilayer wall are described. The multilayer wall may include an inner layer and a sealing layer. The sealing layer is outside of the inner layer and forms a seam around at least a portion of the sample bag. In certain embodiments, the inner layer comprises a patterned periphery. The patterned periphery extends into the seam to provide the inner layer with a mechanical stability.
The inner layer may be a thin metal foil or a plastic film and the sealing layer may include a sealing surface of a thermoplastic, wherein the thermoplastic of each sealing layer may be fused to form a seal around the periphery of the sampling bag. The sample bag thereby an inner layer with a low permeable, low adsorption layer coupled with a second layer providing an effective seal results in a sample bag with improved sample gas stability.

22 Claims, 8 Drawing Sheets

(51) Int. Cl.
*G01N 1/10* (2006.01)
*G01N 1/22* (2006.01)

(56) References Cited

U.S. PATENT DOCUMENTS

| | | | | | |
|---|---|---|---|---|---|
| 4,258,848 | A | * | 3/1981 | Akao | B32B 27/32 206/524.2 |
| 5,239,877 | A | * | 8/1993 | Suddath | B01L 5/02 137/561 A |
| 6,060,096 | A | * | 5/2000 | Hanson | B65D 75/008 219/727 |
| 7,308,783 | B2 | * | 12/2007 | Shepard | B65B 1/188 383/203 |
| 8,002,468 | B2 | * | 8/2011 | Otsuka | B65D 75/5822 383/104 |
| 8,449,187 | B2 | * | 5/2013 | Nakamura | B65D 33/02 383/107 |
| 8,714,035 | B2 | * | 5/2014 | Mihaylav | G01N 1/14 73/864.51 |
| 2003/0228078 | A1 | * | 12/2003 | Clune | A44B 18/0084 383/93 |
| 2006/0000734 | A1 | * | 1/2006 | Ninomiya | A61K 9/703 206/438 |
| 2008/0131636 | A1 | * | 6/2008 | Kinigakis | B29C 47/0021 428/35.7 |
| 2009/0035424 | A1 | * | 2/2009 | Mita | B32B 27/08 426/113 |
| 2010/0220942 | A1 | * | 9/2010 | Nakamura | B65D 33/02 383/89 |
| 2011/0059284 | A1 | * | 3/2011 | Butzloff | B29C 65/04 428/57 |
| 2011/0219891 | A1 | * | 9/2011 | Mihaylov | G01N 1/02 73/864.64 |

FOREIGN PATENT DOCUMENTS

| | | |
|---|---|---|
| KR | 100295597 | 11/2001 |
| WO | 2011106680 A1 | 9/2011 |

* cited by examiner

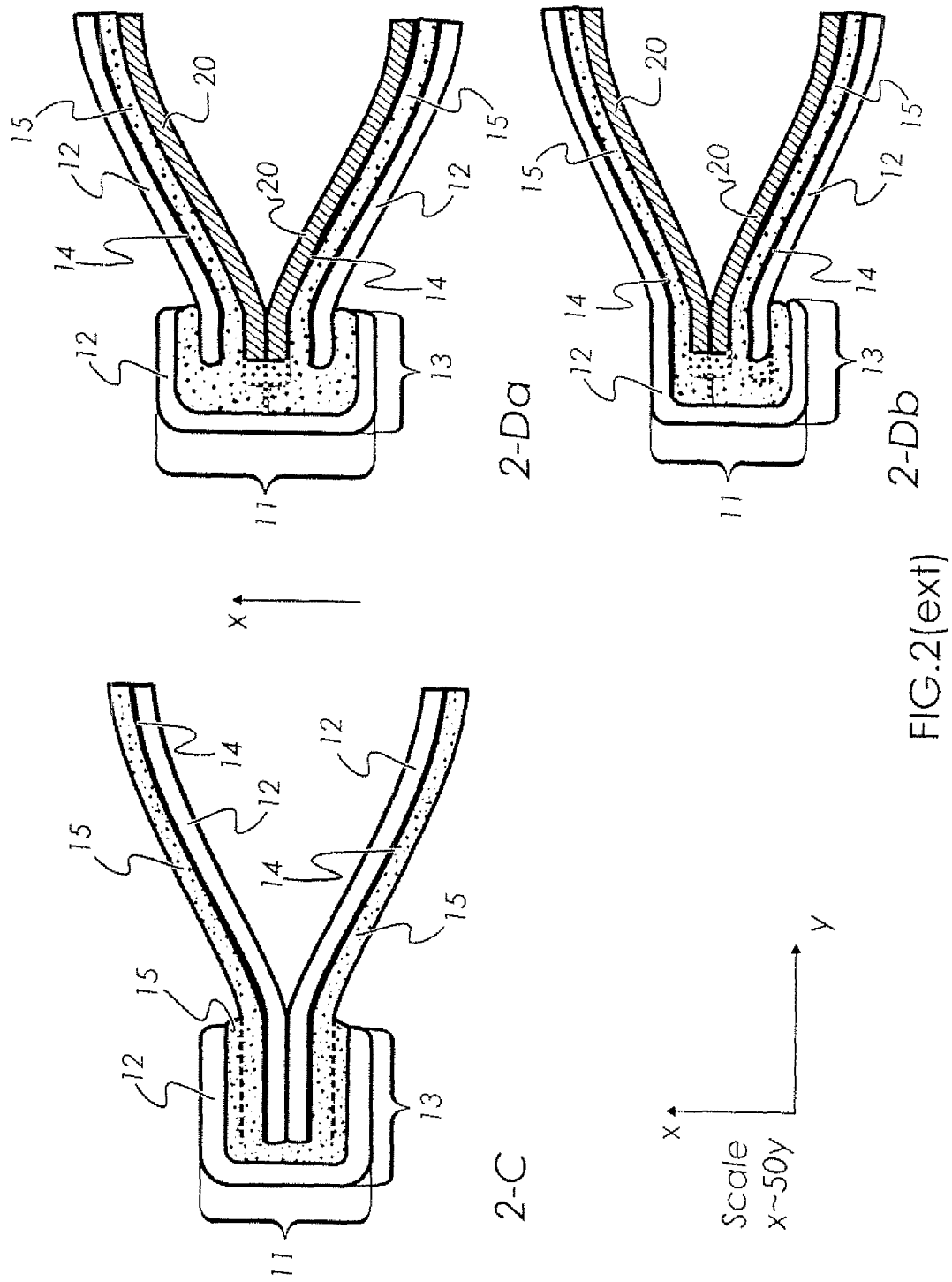
FIG.2(ext)

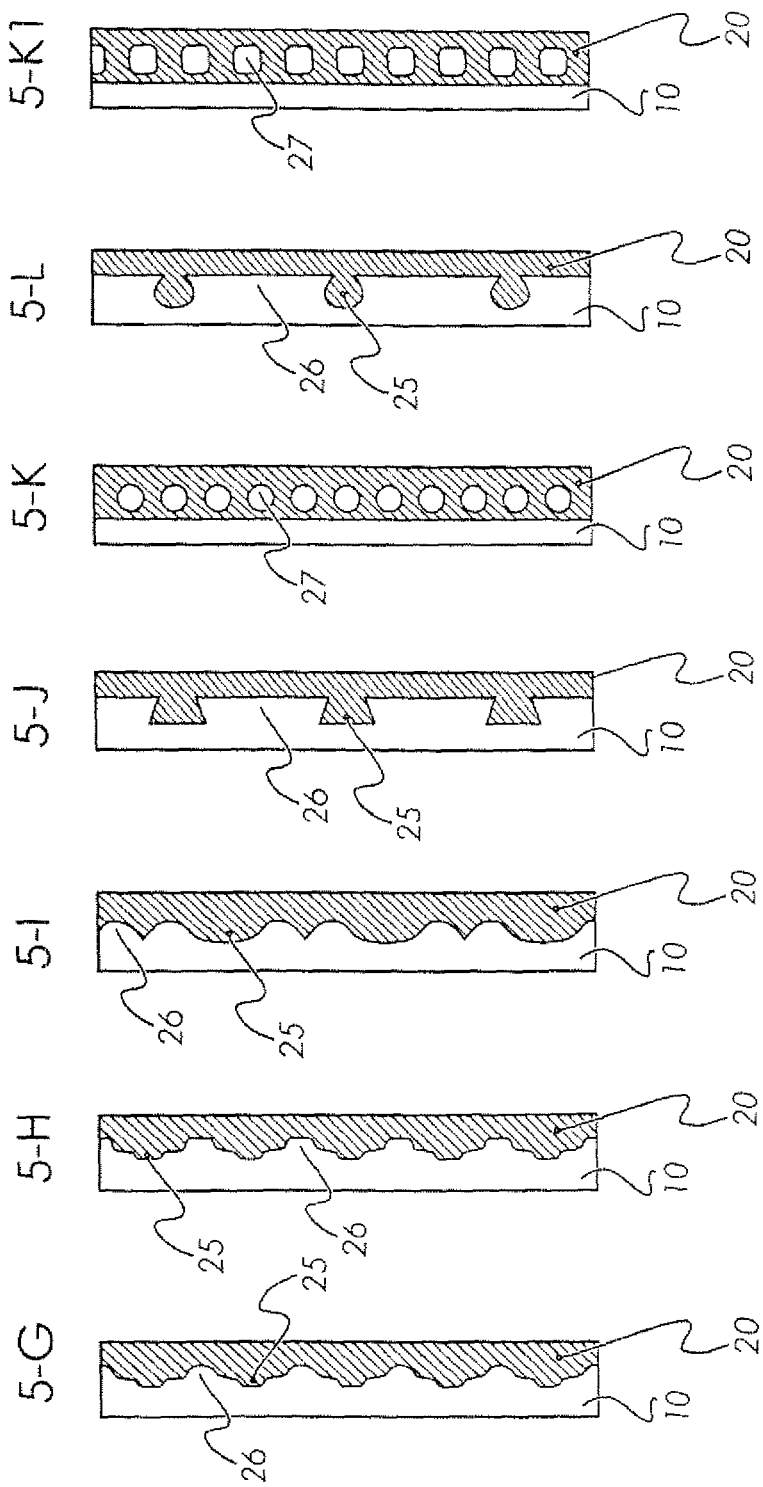
FIG.5(ext)

Fig. 6-A
Fig. 6-B
Fig. 6-C
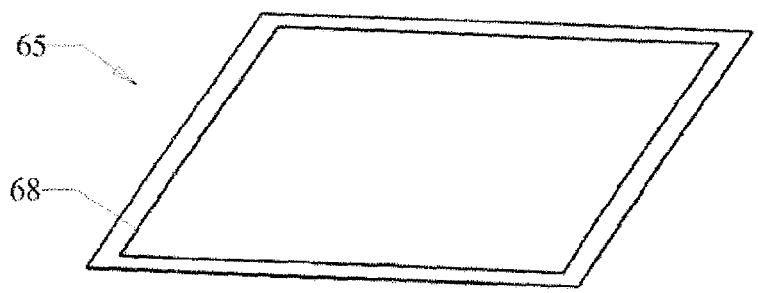
Fig. 6-D
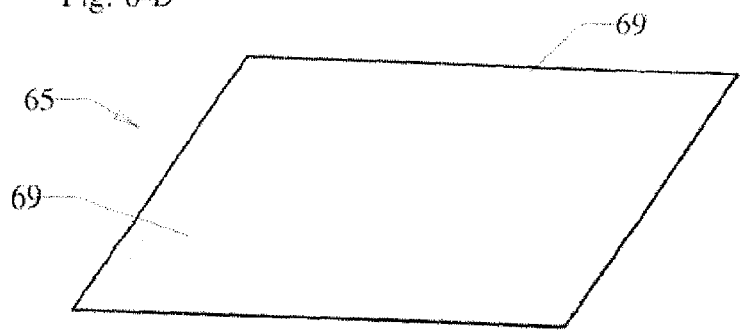
Fig. 6-E

SAMPLING BAG WITH MULTILAYER WALLS

RELATED APPLICATIONS

This application claims priority under 35 U.S.C. 119 to U.S. Provisional Patent Application No. 61/580,863 filed on Dec. 28, 2011 which is hereby incorporated by reference in its entirety.

FIELD OF THE INVENTION

Sampling devices are used with sample bags to obtain samples of fluids and gases (hereinafter "gas" or "gases") to be analyzed to determine the composition of the gas in the sampled environment. Sampling devices may be designed to obtain samples of a gas at a particular moment or obtain a sample over an extended period of time. The sample bags have multilayer walls that provide a high stability of the sampled gas during the sampling process and during storage or transportation of the sample.

BACKGROUND

Gas sampling is regularly performed to determine the amount of various target compounds in an area. The samples may be taken over a short period of time indicating "instantaneous" exposure of personnel to the compounds or taken over an extended period of time indicating the average exposure of the personnel for that period of time. Samples are typically captured in a sample bag with the use of a sampling device comprising a sampling pump.

There are basically two conventional sampling systems, a direct sampling system and an indirect sampling system. A typical direct sampling system is shown in FIG. 1A. As shown in FIG. 1A, a conventional direct sampling apparatus or device 61 comprises a sampling pump 60 that draws a gas to be sampled from the surrounding environment and discharges the sampled gas through the tubing 65 into a sample bag 62. The sample bag 62 comprises an inlet 66 with a tubing connection. The inlet 66 may further be attached to a valve that may be opened during the sampling process and closed to retain the sample in the sample bag 62. The sample bag 62 may then be removed from the sampling device 61 and sent to a laboratory for analysis. In a direct sampling apparatus, the inlet of the sampling pump 60 is in fluid communication with the area to be sampled and the outlet of the pump 60 is in fluid communication with the inner volume of the sample bag 62. As such, the gas to be sampled flows through the sampling pump 60 and tubing 65. In such a direct sampling system, the gas contacts the internal components of the sampling pump 60 and the inner wall of the tubing 65, this contact may result in contamination of the sampled gas or loss of a portion of the sample as it attaches to or reacts with the material in the pump or with the walls of the tubing resulting in a sample that represents less than the actual concentration of the contaminant. The internal components of the pump and inner wall of the tubing may still comprise a residue of previously sampled gas or may be contaminated from a cleaning or maintenance procedures. To eliminate the chance of contamination of the sampled gas and/or loss of a portion of the components of the sampled by contact with the sampling pump or other components of the direct sampling apparatus, indirect sampling apparatuses may be used.

A typical indirect sampling apparatus is shown in FIG. 1B. As shown in FIG. 1B, a conventional indirect sampling apparatus 63 also comprises a sampling pump 60. However, the sampling pump 60 in an indirect sampling method draws air from inside a hermetically sealed box 64 (sometimes referred to as a "lung box") to create a vacuum. A lung box 64 is a rigid walled hermetically sealed box with a connector for the pump 60 inlet and a connector 65 to provide fluid communication between the sample bag 62 with the exterior area to be sampled. A sample bag 62 within the lung box 64 expands due to the vacuum and thus draws gas from the area to be sampled through tubing 65 into sample bag 62. The sample bag 62 in an indirect sampling system also comprises an inlet 66 with a tubing connection and a valve that may be opened during the sampling process and closed to retain the sample in the sample bag 62. The sample bag 62 may be removed from the lung box 64 and sent to a laboratory for analysis. As the pump draws air out of the lung box 64, the walls of the gas-sampling bag 62 are pulled apart by the resultant vacuum thus increasing the inner volume of the sample bag 62 and providing driving force for the ambient gas to be sampled to fill the sample bag 62. The indirect sampling apparatus 63 may be more bulky than a direct sampling apparatus 61 but provides a lower risk of contamination, cross-contamination of samples and/or loss of a portion of the contaminant. Drawbacks for both of the conventional direct and indirect sampling apparatuses include the necessity of carrying and storing bulky equipment, charging the pump batteries, maintaining and calibrating the pump regularly and calibrating the pump by trained personnel before and after use of the pump for time weighted average (TWA) samples, and to establish a clean stationary sampling place. Further, in certain applications such as, but not limited to, chemical, petrochemical, petroleum, and natural gas facilities, the electronic pumps of direct and indirect sampling apparatuses must be certified as intrinsically safe to ensure the electronic pump does not create a spark sufficient to cause an explosion or a fire.

The high prices of both direct and indirect sampling apparatuses and the ancillary equipment affect the overall cost of the sampling. These sampling apparatuses require that the sampling pump be well calibrated and can pump consistently particularly when performing a sampling process through an extended period.

A major drawback of conventional sample bags with thin monolayer walls is their comparably short storage life of a sample retained within the sample bag. Samples may be stored reliably in such sample bags typically from 24 to 48 hrs. or up to 72 hrs. for some specific gases sampled. After this time, the sample gas has changed composition by off-gassing or sorption of components on the interior walls of the sample bag. The stability of a sample and the recovery (%) of target gases is limited by the composition of the inner layer; nevertheless such thin monolayer walls have been developed and are widely used for construction of sample bags.

An advance in sample bag technology was the introduction of multilayer walls for sampling bags. An embodiment of multilayer wall has a sandwich construction comprising at least three layers. The multilayer walls have at least one outer layer comprised of a chemically resistive low permeability material. The multilayer walls have an intermediate layer comprising a thin aluminum layer, wherein the aluminum is provided as a foil or by vacuum metallization process. This aluminum layer slows diffusion through the multilayer wall. The inner layer is a polyolefin layer (typically polyethylene that may be chosen from various density polyethylenes) that serves as a thermal sealing layer. The polyolefins have comparably good barrier properties, but also a tendency to emit (outgas or off-gas) some monomers, plasticizers, and other additives, thereby contaminating the sample. The inner polyolefin layer also has a tendency to adsorb some organics. These drawbacks limit their use mainly to sampling of inorganic gases or to short term sample retention uses. Both single layer and multiple layer walls have inherent permeability and/or sorption which limit the recovery of target gases in the sample to 80-85% and also limit the stability of the sample between 24 to 72 hrs.

Conventional sample bags comprising multilayer materials were adapted from bags developed to meet the requirements and regulations of the food packaging industry. Regulations for bags for food packaging uses allow a certain amount of organics, typically monomers, plasticizers, and/or other additives, to outgas from the plastic. The conventional bag inner layer outgasses certain quantities of compounds that may be acceptable for food storage applications. However, these quantities of outgassed components have the potential to contaminate the sampled gas in a sample. The outermost external layer of conventional multilayer sample bags comprises material that is highly resistive to absorption and diffusion such as polyester and nylon, but these materials have relatively high melting points and therefore are not as desirable as thermal sealing layers. Thus, the outer layer, though it may not be easily sealed together, prevents loss of sample integrity by diffusion through the wall, but the inner layer, which can be easily sealed, results in loss of sample integrity by off-gassing.

A more sophisticated sampling apparatus includes a SUMMA Canister 70 as shown in FIG. 1C. A SUMMA canister is a stainless steel vessel which has specially passivated internal surfaces using a "Summa" passivation process. A Summa passivation process combines an electro-polishing step with chemical deactivation to produce a surface that is chemically inert. Due to the passivation of the surface, chemical compounds are not absorbed on the surface and samples retained in a SUMMA canister are stable for a longer period than a sample retained in a conventional sample bag. To draw a sample into the canister, the pressure within the SUMMA canister 70 is reduced to vacuum of approximately twenty-eight inches mercury to remove substantially all the gas in the canister 70. The residual gas is typically uncontaminated air or ballast such as nitrogen or other inert carrier gas. The SUMMA sampling apparatus comprises a special flow regulator that may be calibrated to achieve predetermined sampling time of, for example, 15 minutes, 30 minutes, 1 hour, 2 hours or up to 24 hrs. The sampling process is typically finished when the pressure in the SUMMA canister has risen to about 2 inches of mercury vacuum; therefore, the canister is still under vacuum even after sampling. To facilitate withdrawal of the sample from the canister for analysis or other use, the SUMMA canister 70 must subsequently be pressurized with an inert carrier gas or filtered calibration grade clean air. The inert carrier gas or filtered calibration grade clean air raises the pressure within the SUMMA canister without contaminating the sample. However, adding gas in the pressurization process and the original gas in the canister after reducing the vacuum to 28 inches results in a dilution of the concentration of the target gases in the sample.

After pressurization, an aliquot volumetric analysis sample of the diluted gas is withdrawn for analysis. Each step including vacuuming, sampling, and pressurizing of the Summa canister is monitored by use of a pressure gauge and the accuracy of monitoring each step depends on the accuracy and reliability of the pressure gauge to calculate volumes of gas in the canister. In many cases, the pressure gauges used with SUMMA canisters do not have accuracy necessary or are not calibrated precisely enough for extremely accurate determination of the dilution ratio between the gas actually sample and the residual gas in the container and the gas added during the pressurization process. Therefore, there is an inherent systematic error in the gas concentration calculations and target gas analytical determination. As such, the accuracy of overall method is compromised from the many steps and is prone to errors.

The disadvantages of using a SUMMA canister sampling apparatus include the initial high costs of the canister, the high cleaning cost of the interior of the canister, high maintenance costs of the canister and peripheral equipment, the high cost of purchasing and maintaining a special cleaning system in specialized labs, the high cost of special gauges and expensive flow controllers, the necessity of a precise flow calibration for each extended sampling period, the necessity of constant observation during a sampling period to end the sampling process so the pressure does not exceed the limit of 2 inches of mercury vacuum, the necessity of accurately pressurizing the SUMMA canister with a carrier gas or filtered calibration grade clean air, the high cost of the inert carrier gas cylinder and cylinder demurrage or the cost of creating the filtered grade clean air, the necessity of performing additional calculations after chemical analysis, and the necessity to know the initial sampling conditions including temperature, barometric pressure, and altitude above sea level.

In accordance with drawbacks discussed above, there is a need for a sampling systems, devices and methods which will eliminate at least a portion of the drawbacks of the conventional sampling methods but still provide the benefits.

There is a need for a sample bag that limits contamination be off-gassing and still prevents loss of sample integrity by diffusion through the sample bag walls or adsorption of chemical compounds on the sample bag walls.

SUMMARY OF THE INVENTION

Accurate environmental sampling requires a sampling device and sample bags that may be used in a manner that does not significantly contaminate the sample while maintaining the integrity of the sample. Embodiments of the sample bags describe herein comprise at least two walls, an inner layer and a sealing layer. The inner layer may be in contact with the sampled gas and does not significantly interact with the sample. In certain embodiments, the material of the inner layer is chosen to maintain the integrity of the sample gas. The sealing layer provides a substantially hermetic seal to the sample bag.

An embodiment of the sample bag comprises at least one multilayer wall. The multilayer wall comprises an inner layer and a sealing layer. The sealing layer is outside of the inner layer with respect to the inner volume of the sample bag and forms a seam around at least a portion of the sample bag. In certain embodiments, the inner layer comprises a patterned periphery. The patterned periphery extends into the seam to provide the inner layer with a mechanical stability.

The inner layer may be a thin metal foil or a plastic film. As examples, the inner layer may comprise an inner surface of stainless steel, aluminum, metal alloy or of polyether-etherketone. Embodiments of the sealing layer may comprise a sealing surface comprising a thermoplastic, wherein the thermoplastic of each sealing layer may be fused to form a seal around the periphery of the sampling bag. The sealing layer may be an intermediate layer between the inner layer and an outermost layer or the sealing layer may be outermost layer. The sealing layer comprises a sealed seam portion with a portion of the inner layer embedded in the seamed portion.

The embodiment of the sample bag comprising an inner layer with a low permeable, low adsorption layer coupled with a second layer providing an effective seal results in a sample bag with improved sample gas stability by minimizing the detrimental effects of a polyolefin inner layer. Additionally, embodiments of the sample bag with an inner layer comprising a more temperature stable material than conventional polyolefins is capable of being cleaned and reused for taking multiple samples.

In another embodiment, a sampling bag may comprise a first multilayer wall comprising a first sealing layer and a first inner wall and second multilayer wall comprising a second sealing layer and a second inner layer. The two sealing layers may be sealed together on their periphery to form a seamed periphery portion.

The first inner layer and a second inner layer may further each comprise a patterned periphery that extends into the seamed periphery portion. The patterned periphery provides at least some mechanical locking of the inner layer in the seamed periphery portion. The patterned periphery may or may not have similar designs.

Embodiments of the sample bag comprise flexible walls. The flexible walls have an inner layer of an impermeable or very low permeable material. The inner layer may also have a high chemical stability and low surface sorption for target gases and vapors. The inner layer is in contact with the target sampled gas and may be substantially chemically inert to the target sampled gas.

Further embodiments of the sample bag may comprise an inner layer of a substantially impermeable material and a sealing layer for sealing the sample bag. In embodiments of the sample bag comprise an inner layer comprising a material that is more difficult to hermetically seal than the sealing layer. In embodiments of the sample bag, the inner layers form wrinkles and/or stress points while the sample bag is repeated inflated and deflated resulting in holes from material fatigue if the inner layers had been seamed directly together. A sealing layer may be laminated at a periphery portion of the inner layer and be sealed around this periphery portion. The sealing layer may be sealed by thermo-sealing, an adhesive, welding, or folding, for example.

For example, the sealing layer may be a polyolefin layer. Polyolefins are stable at ambient and proposed sample bag cleaning temperatures but have relatively low melting points such that the sealing layer may be melted allowing thermal sealing of bag's walls at the periphery.

Embodiments of the sample bags of the invention move the sealing layer from the inner wall as in conventional sample bags to an outer or intermediate layer reducing the potential of out-gas contamination of the sample and sorption of the target gas on the wall on the sample bag. Embodiments of the sample bag comprise multilayer walls. The multilayer walls have a flexible inner layer having substantially no diffusion of the target gases through the wall and minimal surface sorption for target gases. The inner layer may comprise corrosion resistive and chemically stable materials such as, but not limited to, foils of corrosion resistive and chemically stable metals, stainless steels, titanium, titanium alloys, nickel, and/or nickel alloys, for example. Additionally, such materials may be plastics with chemical stability and low diffusive permeability, such as, but not limited to, fluorinated polymers such as, but not limited to, polytetrafluoroethylene (PTFE or Teflon™), polyvinylidene fluoride (PVDF or Kynar™), and polyvinyl fluoride (PVF or Tedlar™), polyether-ether-ketone (PEEK), nylon, polyester, their copolymers and similar plastics. Sheets of PEEK have very low permeability and low surface sorption. PEEK has one of the lowest permeability ratings and lowest outgassing properties of all conventional plastics.

Further, materials such as polyester, nylon and other copolymers having low outgassing and low gas permeability and may be used in many applications to provide superior sample integrity relative to sample bags with polyolefins in the inner layer.

The materials of the inner layer are not readily thermosealed to form a hermetically sealed sample bag due to their relatively high melting points. This limitation previously excluded such materials to be used as inner layer in conventional gas sampling bags.

Embodiments of the sample bags of the invention comprise a flexible multilayer wall with an inner layer surface covered by one of materials such as, but not limited to, the inner layer may comprise corrosion resistive and chemically stable materials such as, but not limited to, foils of corrosion resistive and chemically stable metals, stainless steel, titanium, titanium alloys, nickel, and/or nickel alloys, for example. Additionally, such materials may be plastics with chemical stability and low diffusive permeability, such as, but not limited to, fluorinated polymers such as, but not limited to, polytetrafluoroethylene (PTFE or Teflon™), polyvinylidene fluoride (PVDF or Kynar™), and polyvinyl fluoride (PVF or Tedlar™), polyether-ether-ketone (PEEK), nylon, polyester, their copolymers and similar plastics. Sheets of PEEK have very low permeability and low surface sorption. Contemporary technology of manufacturing allows thin foils of corrosion resistive and chemically stable metals, stainless steels, titanium, titanium alloys, nickel, nickel alloys, as well as films of fluorinated polymers such as, but not limited to, polytetrafluoroethylene (PTFE or Teflon™), polyvinylidene fluoride (PVDF or Kynar™), and polyvinyl fluoride (PVF or Tedlar™), polyether-ether-ketone (PEEK), nylon, polyester, their copolymers and similar plastics. Embodiments of the sample bags would comprise an inner layer of a material with desired chemical, sorption and diffusion properties.

In some embodiments of the sample bag, the dimensions of the inner layer sheets have a smaller surface area than the sealing layer. Further embodiments of the inner layer have a patterned periphery. The pattern periphery may extend into the thermal sealed seam of the sealing layer comprising a polyolefin.

In some embodiments, the material of the inner layer may have very little or no inherent adhesion to polyolefins. The patterned periphery may comprise teeth protruding into the seamed portion. The width of the seam allows the teeth to extend into the seamed portion but not to protrude from the outer edge of the sample bag. The shape and the actual length of the teeth may be any length that allows the periphery to be retained in the seam without protruding through the seam. The number of teeth, distance between the teeth, length of the teeth, the width of the seam, the material of the sealing layer may depend on the properties of the inner layer. The design of the patterned periphery may be sufficient to keep the inner layer mechanically connected within the sealing layer.

When the inner layer is sealed on the edges with the outer layer the distance between the layers is small and there is minimal air or other gas which may expand under vacuum. Then when such a bag is filled through the inlet with a sample, the inner layer behaves as an integral part of the multilayer wall.

A device incorporating the present invention advantageously avoids drawbacks of existing sampling bag or canister sampling methods and devices. The device is easy to manufacture. The device may be reused after thermal cleaning or other applicable cleaning technique, for example. Thermal cleaning may be accomplished with hot air similar to the process used for SUMMA canisters. The inner wall, in some embodiments, may withstand cleaning temperatures up to or more than 80° C. Reuse makes the sample bags more versatile and less expensive to use over their life cycle.

Other aspects and features of embodiments of the sampling bags comprising a sealing layer and an inner layer will become apparent to those of ordinary skill in the art, upon reviewing the following description of specific, exemplary embodiments of the present invention in concert with the figures. While features may be discussed relative to certain embodiments and figures, all embodiments can include one or more of the features discussed herein. While one or more particular embodiments may be discussed herein as having certain advantageous features, each of such features may also be integrated into various other of the embodiments of the invention (except to the extent that such integration is incompatible with other features thereof) discussed herein. In similar fashion, while exemplary embodiments may be discussed below as system or method embodiments it is to be understood that such exemplary embodiments can be implemented in various systems and methods.

BRIEF DESCRIPTION OF THE DRAWINGS

FIG. 1-B depicts a conventional indirect sampling apparatus for direct short or long term sampling comprising a variable speed pump connected to a hermetically sealed box with rigid walls and a sample bag within the box with inlet in fluid communication through one of the walls with the ambient air; FIG. 1-C depicts a conventional SUMMA canister apparatus with a fluid flow controller/regulator and pressure gauge;

FIG. 2-A depicts a seam of a conventional multi-layer sample bag comprising an inner thermoplastic layer that is fused together to form a seal and two additional layers to provide the desired properties to the wall and FIGS. 2-B, 2-C, 2-Da and 2Db depict embodiments of sample bags comprising an inner layer with a patterned periphery and an outer layer that forms a seal around the perimeter of the sample bag;

FIGS. 5, 5A, 5B, 5C, 5D, 5E, 5F, 5G, 5H, 5I, 5J, 5K, 5 K1, and 5L depict several possible embodiments of the patterned periphery including shapes of the teeth, apertures, scalloping, and other shapes; and FIG. 6-A depicts a cross-sectional view of an embodiment of the inner layer comprising a folded edge; FIG. 6-B depicts a cross-sectional view of two inner layers of FIG. 6-A positioned adjacent to each other in a face to face relationship with the folded edges positions on opposites sides; FIG. 6-C depicts a cross-sectional view of an embodiment of the inner layer comprising an indentation; FIG. 6-D depicts a perspective view of an inner sheet comprising linear indentations adjacent to all four edges of the inner layer; and FIG. 6-E depicts a perspective view of an inner sheet comprising a plurality of indentations adjacent to all four edges of the inner layer;

DETAILED DESCRIPTION OF THE DRAWINGS

Figure 1:
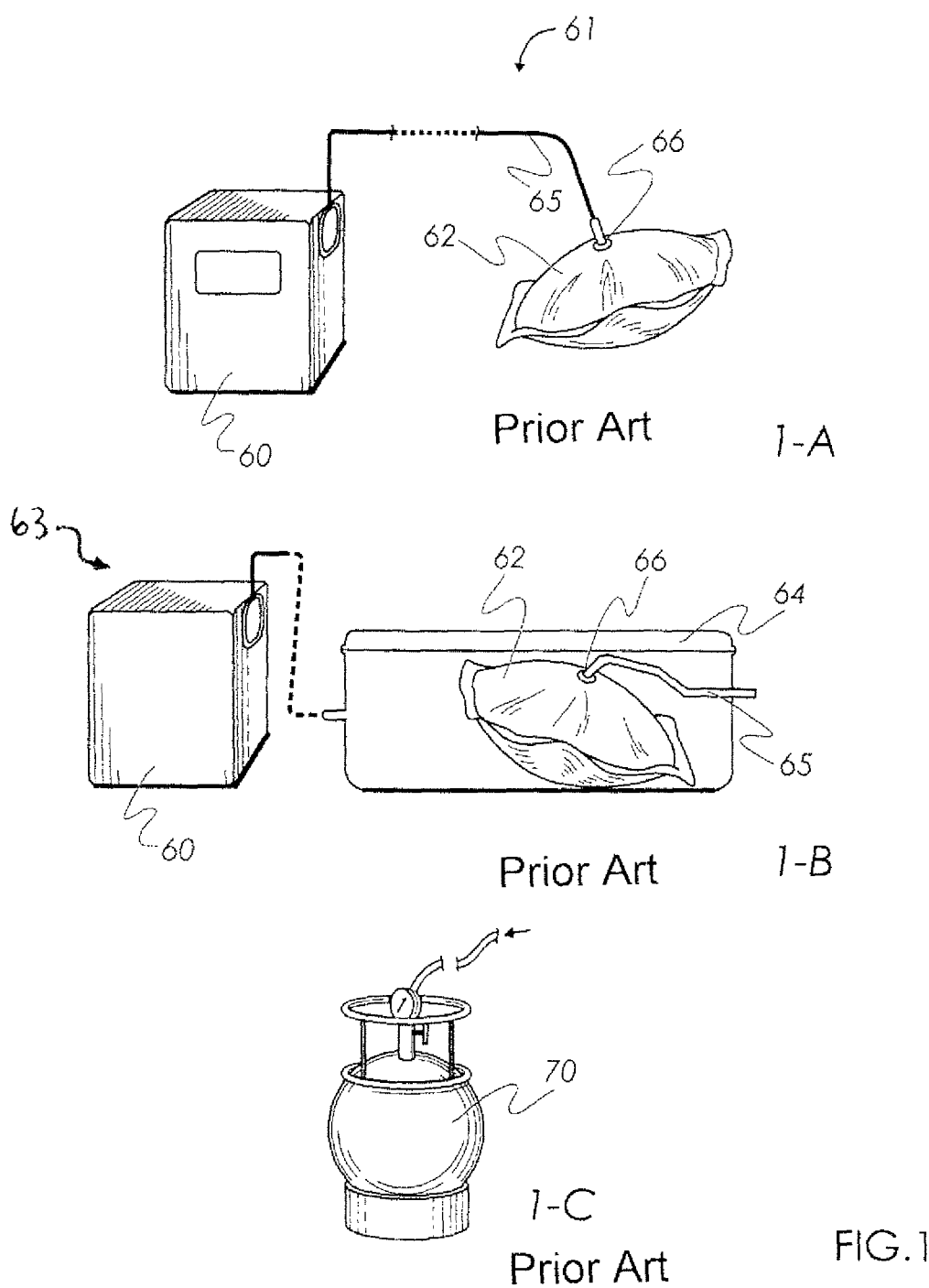
FIG. 1 depicts three conventional sampling devices, wherein FIG. 1-A depicts a conventional direct sampling apparatus capable of direct short or long term sampling comprising a variable speed pump pumping a sample into a gas-sampling bag.

Industrial hygienists and other professionals use sample bags to collect and retain samples from a work environment to determine the concentration of target gases in the air or other environment. Preferably, the sample bags are substantially impermeable to the components of the sampled gas, will not contaminate the sampled gas by, for example, off-gassing of components of the inner wall, and will not absorb and/or adsorb target gases on their surface so that that the sampled gas remains unadulterated and accurately represent the concentration of gases in the sampled environment at the time of analysis. Off-gassing of components of the inner wall of the sample bag into the sampled gas can contaminate the sample resulting in uncertainty between the concentration of components in the sampled environment and additional gases added to the sample from the walls of the sample bag. Conversely, sorption of components of the sample gas on the walls of the sample bag results in a reduction of concentration of the absorbed gases when the sample is analyzed as components are removed from the sample. Both of these processes change the composition of a retained sample over time. Therefore, industrial hygienists attempt to analyze a sample shortly after the sample is taken to mitigate errors resulting from retaining the samples in the bags and to provide the most accurate sample results.

Embodiments of the sample bags comprise two multilayer walls. The multilayer walls may be the same or different. The multilayer walls may comprise an inner layer and a second layer. The second layer may be a sealing layer that is capable of forming a substantially hermetic seal for the seams of the sample bag. An embodiment of a sample bag comprising an inner layer with a low permeable, low adsorption layer coupled with an effective sealing layer not substantially in contact with the sample results in a sample bag with improved sample gas stability by minimizing the detrimental effects of a polyolefin inner layer. Additionally, embodiments of the sample bag with an inner layer comprising a more temperature stable material than conventional polyolefins is capable of being cleaned and reused for taking multiple samples.

In embodiments of the multilayer wall, the second layer may be an intermediate layer between the inner layer and an additional outer layer or the second layer may be the outer layer.

Sample bags typically comprise a sealed bag comprising an aperture, an inlet is sealing connected through the aperture such that there is no significant leakage around the inlet, and a valve connected to the inlet such that when the valve is closed the sample bag is hermetically sealed. Conventional sample bags typically have an inner polyolefin layer that is thermo-sealed to seal the walls together and create the sample bag. However, an inner polyolefin layer creates the off-gassing and sorption problems as described above. Polyolefin off-gases include, but are not limited to, residue monomers and processing agent, for example. Further, active sites on the polyolefins or and voids in the polymeric network may provide sites for sorption and diffusion of chemical compounds from the sampled gas. However, polyolefins are thermoplastics and provide a simple, inexpensive method of sealing to form a hermetically sealed bag, therefore, sampling bags with polyolefin inner layers have been adopted by industrial hygienists whereby disadvantages are minimized by retaining samples in the polyolefin inner wall bags for a short time.

Embodiments of the sample bag significantly reduce the problems created by off-gassing, sorption and diffusion of sample gas components on or through the walls but retain the advantages of a polyolefin or thermoplastic layer in the sample bag. To provide these advantages, embodiments of the sample bags do not include an inner wall consisting of polyolefins. Though there may be a periphery portion of the inner volume of the sample bag that is exposed to a polyolefin of an intermediate or outer layer, the inner wall is substantially comprised of a substantially impermeable, non-off-gassing and low sorption material.

The intermediate layer as described herein may not necessarily be the inner-most layer, but is closer to the inner volume of the sample bag relative to the second layer. The inner layer is the inner most layer of the sample bag such that the inner surface of the inner layer would be in contact with the sampled gas after sampling.

As such, an embodiment of a sample bag may comprise a first sealing layer and a second sealing layer. The two sealing layers may be sealed together on their periphery to form a seamed periphery portion. This sealed periphery portion may be similar to conventional sample bags comprising a polyolefin inner layer. The patterned periphery of the inner layer at least partially extends into the seamed portion of the sealing layers. For example, in one embodiment, the inner layers of the sample bags are thin stainless steel sheets or foils. In other sampling bags, the thin stainless steel sheets may be sealed along there periphery or through their patterned periphery by a welding process as described in U.S. patent application Ser. No. 13/035,163, which is hereby incorporated by reference.

Alternatively, the stainless steel sheets may be sealed together by laminating a two stainless steel sheets between two thermoplastic sheets, a thermoplastic sheet folded around the patterned periphery or one thermoplastic sheet and a material that will seal with a thermoplastic sheet. As used herein, a "thermoplastic sheet" is a sheet comprising at least one thermoplastic material on an outer surface. The sealing layers have a greater surface area than the stainless steel sheet and extend beyond the edges of the stainless steel sheet. The exposed edges of the sealing layer, thermoplastic sheet, or, in one embodiment, polyolefin layer, may then be thermo-sealed or otherwise sealed to another sealing layer to form a sample bag with two stainless steel inner layers and two sealing layers. In one embodiment as described, the two sealing layers comprise a polyolefin that is thermo-sealed around the perimeter to form the sample bag. Both the sealing layer and the inner layer at least on one side of the bag comprise corresponding apertures to allow a sample gas to be pumped or otherwise drawn into a inner volume defined between the two inner layers. In such an embodiment, the stainless steel provides an improved inner layer to conventional polyolefin layers while retaining the effectiveness of a polyolefin sealing layer.

In specific embodiments of the sample bags, the inner layer has a patterned periphery. The patterned periphery comprises a shape or shapes that are not simply linear between corners, have rounded corners, or a simple circular shape for round sample bags. A patterned periphery may comprise a plurality of teeth, for example. Further, for example, the patterned periphery may have a plurality of undulations, extensions, apertures, tongues, teeth or other components that may extend into the seamed portion of the sealing layer and are sufficiently engaged by the seamed portion to withstanding the forces of inflating the sample bag and retain the periphery of the inner layer within the seamed portion of the sealing layer. As used herein, these components, undulations, extensions, apertures, tongues, or teeth may be referred to, individually as a "tooth" or collectively as "teeth."

In embodiments of the sample bag, the sealing layer comprises a seamed portion around at least of a portion of the periphery of the sample bag and the patterned periphery extends into the seam portion. As used herein, the term "patterned periphery" means a periphery that comprises a plurality of components, protrusions, apertures, or teeth protruding from the edge and does not necessarily mean that the component, protrusion, aperture, or tooth is part of a repeating or regular sequence.

Figure 2:
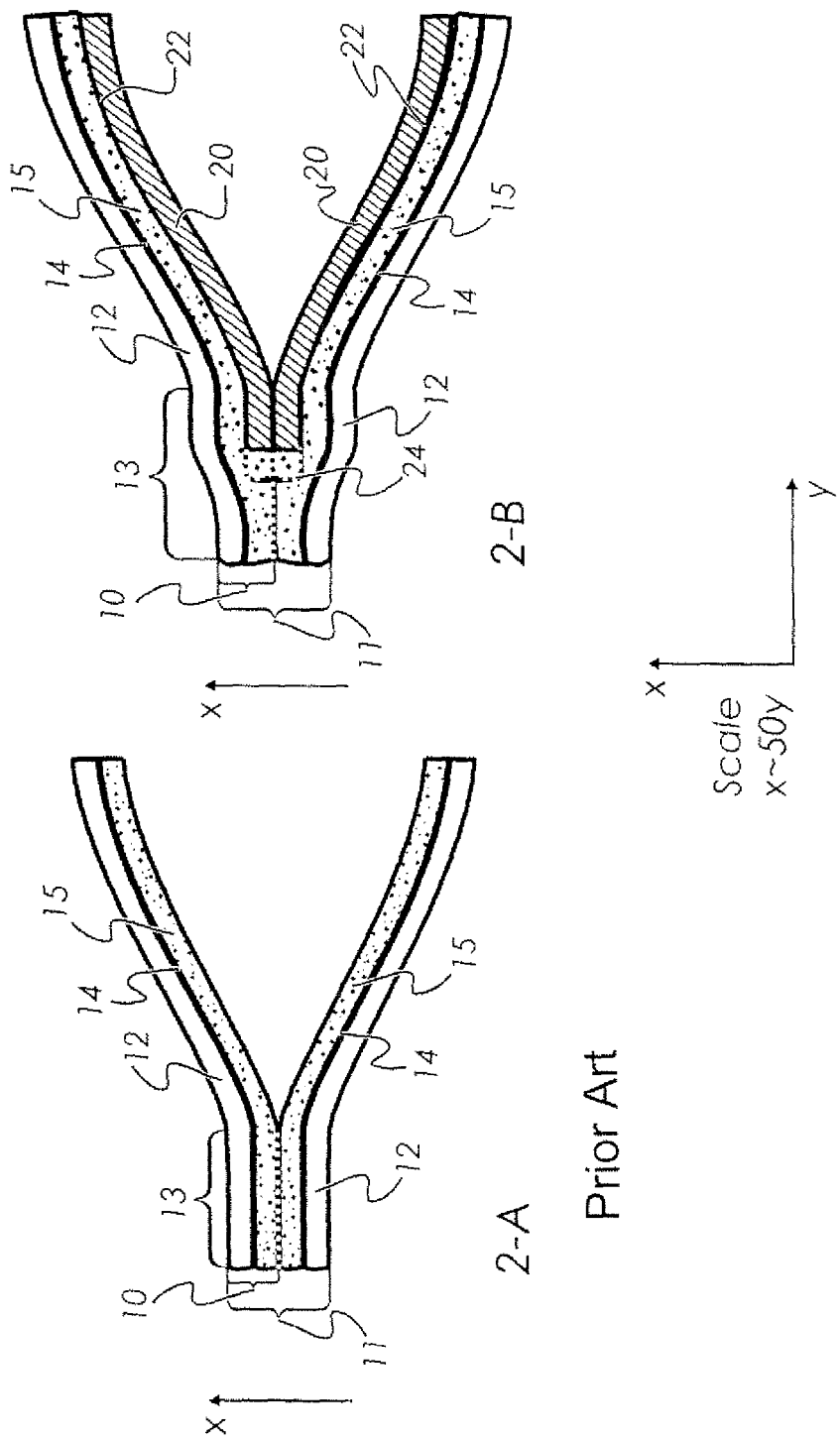
FIG. 2.

FIG. 2-A depicts a portion of a conventional sample bag. FIG. 2-B depicts an embodiment of the sample bag comprising an inner layer with a patterned periphery. Specifically, FIG. 2A depicts a cross-sectional view of a portion of a conventional sample bag A. Sample bag A comprises a multilayer wall 10 comprising an inner layer 15 and an outer layer 12. The inner layers 15 of conventional multilayer sample bag typically comprise a polyolefin that is sealed around a periphery 13 to form the sample bag. The multilayer wall 10 of the conventional sample bag A may additionally comprises an intermediate layer 14 comprising aluminum. The aluminum layer may be formed directly on another layer by a deposition process or added between the layers as a thin sheet of aluminum. The three layers, the inner layer 15 of a polyolefin, the intermediate layer 14 of aluminum, and the outer layer 12 of nylon or polyester in combination form one multilayer wall 10 of the conventional sample bag A. The polyolefin inner layers of two multilayer walls 11 may be sealed together to form a sealed periphery 13. In such configurations, the inner layers 15 of polyolefin are thermo-sealed together by a simple heat treatment to form the hermetically sealed sample bag. Polyolefins have melting points that are in a desired range for sealing sample bags. The melting points are above cleaning and sampling temperatures but low relative to other materials. For example, common commercial grades of medium- and high-density polyethylene have a melting point typically in the range 120 to 130° C. (248 to 266° F.), while the melting point for average, commercial, low-density polyethylene is typically 105 to 115° C. (221 to 239° F.). Typical grades of polypropylene have a melting point in the range of 130 to 171° C. (266-340° F.). As such, these polyolefins are easily handled and thermo-sealed.

In such a conventional sample bag A, the combination of three layers creates an acceptable sample bag with certain limitations as discussed above. For example, the inner layer 15 of polyolefin may be sealed creating a hermetically sealed sample bag, the intermediate layer 14 of aluminum creates an impermeable layer, and the outer layer 12 provides a toughness and strength to the sample bag. The inner layer 15 does provide an effective sealed perimeter against leakage, however, the polyolefins will off-gas contaminants and adsorb and/or adsorb sampled gas components onto the surface and into the polymeric network. Thus, the positive qualities of the inner layer 15 are at least partially off-set by the detrimental effects of the stability of a sampled gas retained in the conventional sample bag.

The embodiment of the sample bag B depicted in FIG. 2B provides a solution to the problems and detrimental effects of the conventional sample bag A. The inventors have determined that a sample bag with a low permeable, low adsorption layer as the inner layer coupled with a second layer providing an effective seal provides a sample bag with improved sample gas stability by minimizing the detrimental effects of a polyolefin inner layer. Additionally, embodiments of the sample bag shown in FIG. 2-B may be capable of being cleaned and reused for taking multiple samples.

The embodiment of the sample bag B comprises an inner layer 20 of a metal foil, metal sheet, or plastic film. The inner layer 20 of a metal foil, metal sheet or plastic film may be selected from a group of thin corrosive resistive metal foils such as, but not limited to, a stainless steel (SST), titanium, titanium alloys, nickel, nickel alloys, or similar metal sheet or foil having relatively low outgassing and diffusive penetration or thin plastic films such as, but not limited to, nylon, polyester and their copolymers or a group of materials superior to olefins as non-diffusive penetrating and substantially no outgassing such as nylon and polyester. These plastics may not have the advantageous thermo-sealing properties of a thermoplastic or polyolefin, but have chemical characteristics that provide stability to a retained sample.

In a specific embodiment, the inner layer 20 is a stainless steel such as a stainless steel alloy selected from a group comprising SST 304, SST 304L, 309, SST 309L, SST 316, SST 316L, SST 321, SST 321L and low carbon stainless steels. Additionally, the inner layer may comprise an inner surface of PEEK.

In certain embodiments, the inner layer 20 comprises a patterned periphery 24. The patterned periphery 24 (shown in dashed lines) extends into the seamed portion 26 of the multilayer wall 10. The gas sample bags have the improved properties by replacing the inner polyolefin layer of conventional sample bags with more chemically stable and inert materials without sacrificing the ease of sealing of polyolefin layers. In such improved sample bags, a gas sample retained in the sample bag has increased chemical component stability relative to conventional flexible, sample bags and comparable stability of a sample retained in a "summa canister." However, the sampled bag is much lighter and cheaper to purchase and maintain as compare to "summa canisters." As with "summa canisters," embodiments of the sample bag with an inner layer having a patterned periphery may be cleaned by heating and flushing with clean air. As the inner layer of embodiments of the sample bags will not outgas at the temperatures typically used for cleaning "summa canisters," a cleaning temperature between 70° C. to 80° C. may be safely used to remove residue of previous sampling from an embodiment of the sample bag comprising a metal alloy inner layer.

The inner layer of the sample bag may be any thickness that provides the desired impermeability and flexibility. For example, embodiments of sample bag may have an inner layer having a thickness between 10 microns to 100 microns; in other embodiments the inner layer may have a thickness in a range from 25 microns to 50 microns.

The inner layer, outer layer or sealing layer may be a multilayer in itself or may be a single layer with consistent composition. For example, the outer layer 12 and/or 14 may be the same multilayer wall as shown and described in FIG. 2-A or it may be used as an inner layer with the polyolefin sealing layer on the exterior and extending beyond the edge of the other layers to form a thermo-sealing periphery. In such an embodiment, the outer layer or sealing layer 10 comprises an inner or exposed surface comprising a thermoplastic. The second layer may not be a complete layer but may only be a partial layer around the periphery of the sample bag as shown in FIGS. 2-C and 2-Da. In such an embodiment, the sealing layer 12 may merely overlay the patterned periphery 24 as shown in FIG. 2-B. In embodiments of the sample bag, the sealing layer 2 comprises a thermoplastic that has adhesiveness with the inner layer sufficient to create a hermetic seal between the layers. The thermoplastic of each sealing layer is fused to form a seal or seam 13 around the periphery of the sampling bag and to adhere to the inner layer 20, wherein a portion of the patterned periphery 24 of the inner layer is between two layers of thermoplastic. See FIGS. 2, 3, 4, and 5, for examples. The term "layers" is used generally, the thermoplastic may be fused together by a thermal process into a single structure but is still considered to be two layers as at least a portion of the thermoplastic is on either side of the inner layers.

The thermoplastic of each layer are fused in the seamed periphery portion; thus forming a hermetically sealed sample bag. The thermoplastic may be, but is not limited to, one of polyethylene, polypropylene, copolymers of polyethylene and/or polypropylene, copolymers derived from at least one olefin monomer, or a combination thereof. In preferred embodiments, the pattern periphery is mechanically locked in the seamed periphery portion.

In certain embodiments, the patterned periphery of the inner layer 20 extends into the seam 11 and the seam portion 13; however, the inner layer 20 does not extend through the seam 11 reaching the outer edge of that seam portion 13. The inner layer 20 has its patterned periphery extending into the seam 11 without extending through the sealed seam portion 13. In the embodiment shown in FIG. 2-Db, one sealing layer 15 is folded over the end of the seam 11 and thermo-sealed to the other sealing layer 15 to ensure the teeth do not extend from the seamed portion 13. In some embodiments, the inner layer and outer layers are not connected, attached, or otherwise adhered together outside the seamed portion 13 and/or an area surrounding an inlet or valve. As such, there may be some of air present between the layers. During the sealing process, any gas reaching the inner sampling bag space may exert pressure on the layer therefore keeping the inner layer 20 in close proximity to the outer wall 10. After the sealing process, there is little or no air between the inner layers and the sealing layer or other intermediate layer. Thus, the multilayer walls with inner layer 20 have a certain degree of integrity even without an adhesive between the inner layer 20 and outer layer of the wall. Other embodiments may comprise an adhesive 22 between the inner layer 20 and the outer layer 12. The adhesive layer 22 may be used to maintain the layers in proper configuration in the sealing process or may be helpful to eliminate air pockets between the layers of the sample bag, for example. In some embodiments, the adhesive may have extremely low outgassing properties.

Figure 3:
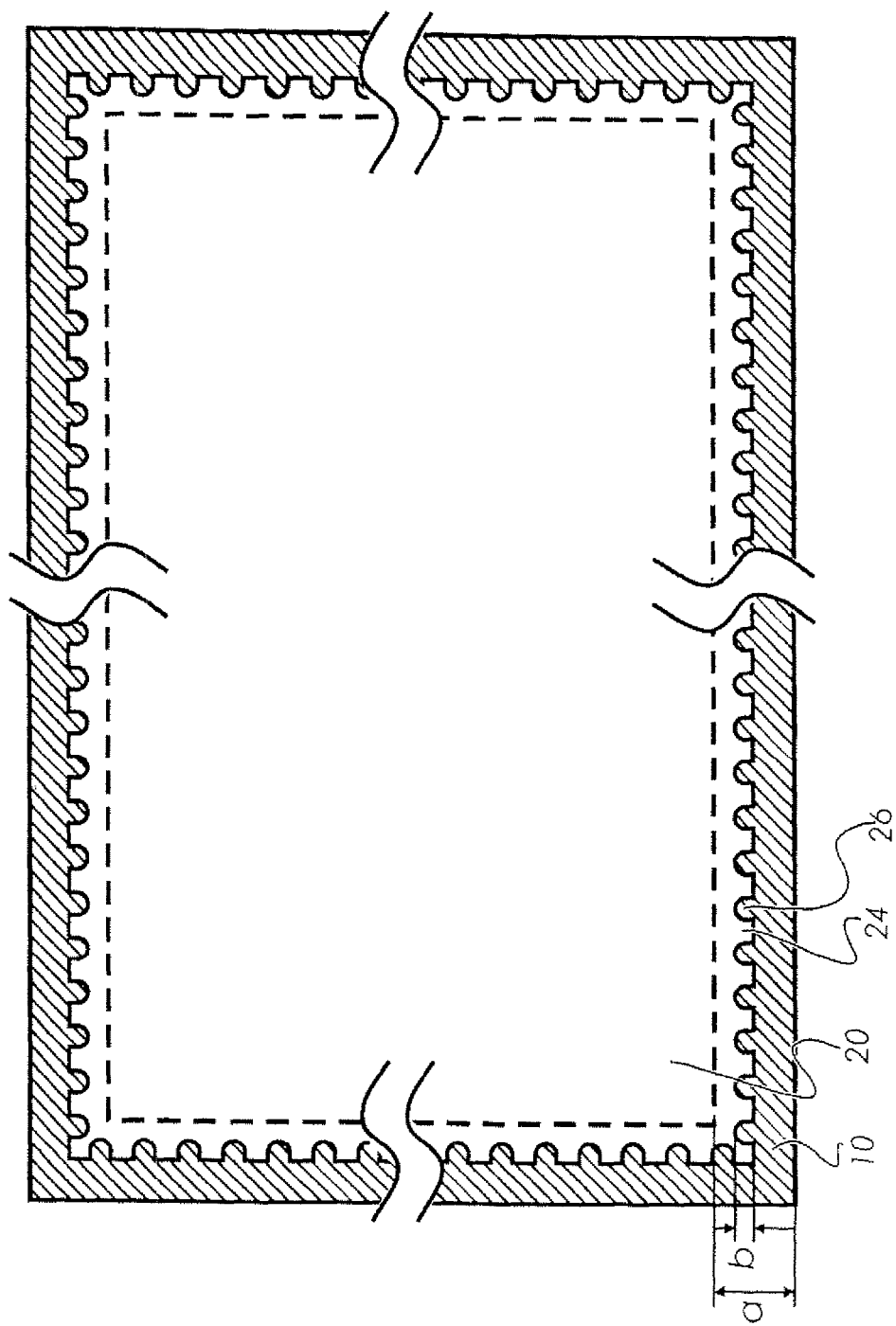
FIG. 3 depicts an embodiment of a single multilayer wall comprising a thermoplastic layer 10 and an inner layer 20 with a patterned periphery covering the entire perimeter of the inner layer.

In some embodiments as shown in FIG. 3, the inner wall layer 20 including the patterned periphery 24 has length and width dimensions smaller than the outer wall 10. The patterned periphery 24 has components 25 are shaped as small tongues or teeth. In particular embodiments, the periphery of the inner layer 20 may have apertures providing the same benefits of space 26 between the teeth 24 to accommodate the melted sealing portions of layer 10 and provide at least a mechanical locking of the teeth 24 in the seamed portion.

During the sealing process the thermoplastic in area 26 between teeth 24 or in the apertures is fused with melted sealing layers 10 from the top and bottom sealing layers 10. The area of fused thermoplastic overlaps partially the base of the teeth 24, forming a hermetically sealed seam 11 (See FIG. 2, for examples) inside of the sealing layer 10 of the sample bag. The teeth 25 or apertures may be distributed equidistantly around the patterned periphery or randomly on the patterned periphery of the inner layer 20. There should be sufficient number of teeth or apertures to lock or retain the patterned periphery within the seamed portion 13 (See FIG. 2, for examples) of the outer layer 10 at forces developed by inflating the sample bag. The shape of the teeth 24 may be different depending on the properties of the particular material used in the layers or the location on the inner layer. Some exemplary shapes of teeth and apertures are shown in FIG. 5 to illustrate a few possible variations of shapes.

In certain embodiments, the length "b" of the teeth 24 may be approximately half of the width "a" of the seam. Further, in embodiments, the top wall and bottom wall inner layers 20 have similar dimensions and similar teeth cut in the same pattern. Both inner layers 20 may be cut at the same time to produce matching patterned peripheries of their teeth 25 so they may be aligned during the sealing process. If the teeth 24 are aligned, the area 26 between the teeth 24 is maximized and may be filled with the melted and fused sealing layer 15 of the outer wall 10. The two inner walls 20 are shown with aligned teeth 24 in FIG. 4. The teeth 24 may be aligned and held in place prior to sealing by an adhesive or welding, for example. In other embodiments, the teeth of the patterned periphery may not be aligned; the teeth of the top inner layer may alternate with the teeth of the bottom layer, for example.

Figure 4:
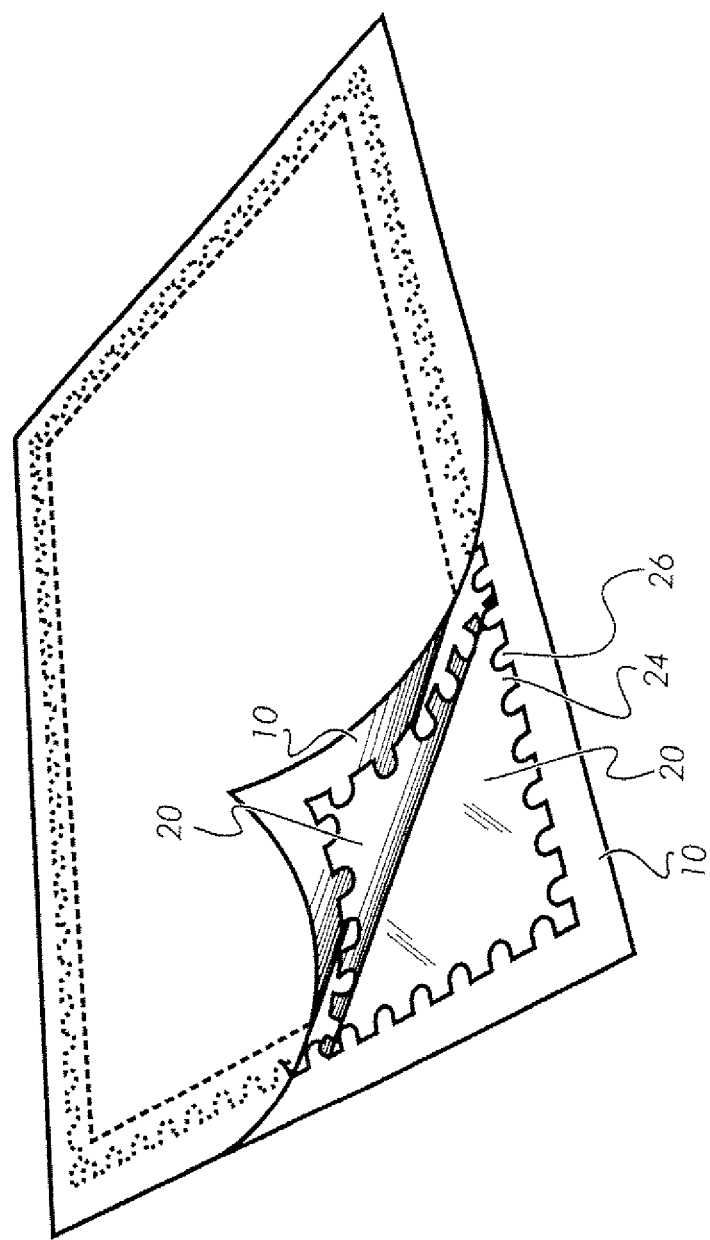
FIG. 4 depicts an embodiment of two multilayer walls comprising a thermoplastic layer 10 and an inner layer 20 with a patterned periphery, wherein the patterned periphery of the inner walls is substantially aligned prior to thermo-sealing to allow the thermoplastic layer to fuse between the elements of the patterned periphery.

In the embodiment shown in FIG. 4, the width of each tooth 24 is less than the width of the area 26 of melted layer between the teeth 24. In a typical embodiment, the seam portion may be any width capable of securing the teeth 24 within the seam 13 (See FIG. 2, for examples); a seam may be between 5 and 10 mm for a typical sample bag. However, other embodiments may have narrower or wider seams. The width of the seamed portion is defined by the width of the heated portion during the thermo-sealing process or the width of the adhesive used to seal the sealing layers. Further, the teeth 24 may be locked by folding or welding their edges in the seam portion 13 to hold the inner layers in position.

Figure 5:
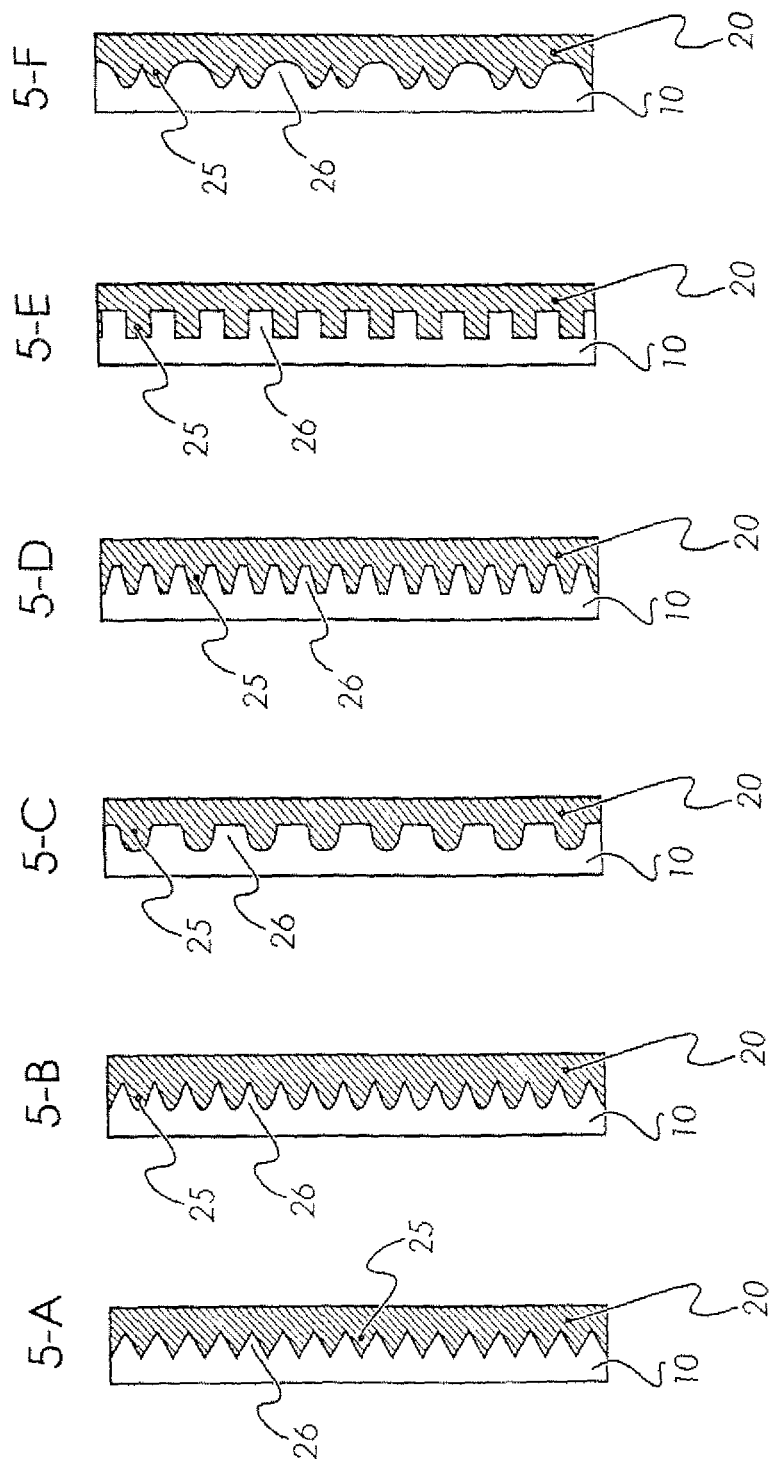

FIG. 5 depicts several shapes of the possible teeth 25 of the patterned edge of the inner layer 20. FIG. 5A depicts a patterned edge comprising a plurality of jagged edge with triangular shaped teeth, FIG. 5B depicts a patterned edge comprising a plurality of rounded teeth, FIG. 5C depicts a patterned edge comprising a plurality of rounded teeth separated by straight sections, FIG. 5D depicts a patterned edge comprising a plurality of trapezoid shaped teeth, FIG. 5E depicts a patterned edge comprising a plurality of rectangular or square shaped protrusions, FIGS. 5F and 5I depict a patterned edge comprising a plurality of rounded or scalloped shaped protrusions, FIGS. 5G and 5H depict a patterned edge comprising a plurality of stepped teeth including plateaus, FIG. 5J depicts a patterned edge comprising a plurality of dove tailed shaped protrusions, FIGS. 5K and 5K1 depicts a patterned edge comprising a plurality of circular apertures, and FIG. 5L depicts a patterned edge comprising a plurality of knob shaped protrusions with a wider head connected by a narrower post. As used herein, a dovetail means a shape that is narrower at a portion closest to the center of the layer and wider at the end to facilitate mechanically retaining the tooth within the seam.

Engineering considerations such as the thickness of the sealing layer, the melting point of the thermoplastic material and the adhesive forces between inner layer and sealing layer are factored into the choice of the shape of the teeth as shown or similar to those shown in FIG. 5 or other shapes. Cutting of the patterned periphery may be performed by stamping, cutting with a knife or other blade, rule die cutting or using scissor edge cutting tools with the desired shape, laser cutting, abrasive water cutting or other methods. The apertures for a valve, a septum, and/or other access point (not shown on pictures) may be cut before or after forming the patterned edges. In certain embodiments of the method of forming the sample bag, the valve and/or septum are mounted into the apertures and then the sealing process is performed and seam 11 produced.

Embodiments of the sample bag may further comprise other means to secure the inner wall in the perimeter seam. The inner wall 60, for example, may alternatively comprise a folded seam 61 as shown in a cross-sectional view in FIG. 6-A. The folded seam of the inner layer may then be sealed in the seam of the sealing layer. The two inner layers may be folded over to form a folded edge. The inner layers may then be placed face to face. In one embodiment, the folded edges are placed on opposite sides as shown in FIG. 6-B. Embodiments of the sample bag may comprise an inner layer that has a plurality of teeth that are folded back upon the layer. The folds of the inner layer may be opposite as shown in FIG. 6-B or nested within one another. Nested folds may be formed by folding the layers independently and subsequently one layer is nested within the other or the two layers may be folded simultaneously.

Another embodiment of the sample bag comprises an inner wall comprising an indentation or a plurality of indentations. The indentation may be at least one linear indentation or a plurality of point indentations adjacent to the edges of the inner layer sheet or foil. An embodiment of the inner layer 65 comprising at least one indentation 66 is shown in a cross-sectional view in FIG. 6-C. The indentation 66 may extend through the sheet or foil as shown or may only form a recess in the surface of the sheet or foil. As in the folded edge embodiments, two inner layers 65 comprising indentations 66 may be nested wherein the protruding portion 67 of the indentation 66 on the first inner layer 65 is received with the recessed portion 68 of the indentation on the second inner layer.

Another embodiment of the sample bag comprises an inner wall 65 comprising a linear indentation 68 on each side adjacent to the edge. The linear indentations may be complete from adjacent to one edge to the other edge as shown in FIG. 6-C. The linear indentations may also be a series of indentations with spaces between the linear indentations without an indentation. Another embodiment of an inner layer 65, shown in FIG. 6-E, comprises a series of point indentations 69 adjacent to an edge of the inner layer 65. The plurality of indentations 69 may be nested as described above in FIG. 6-C or positioned opposite as shown in FIG. 6-B. The indentations may be points, circular shaped, square, rectangular, triangular, or other shape.

Embodiments of the inner layer may comprise a plurality of teeth, apertures, indentations or combinations thereof. These features may be present in any amount required to hold the inner layer stable within the sampling bag. For example, in one embodiment, the inner layer may comprise these features at least one feature per side adjacent to the edge of the inner layer. In other embodiments of the sample bag may comprise an inner layer having features from one feature per inch to twelve features per inch. In other embodiments of the sample bag may comprise an inner layer having features from three features per inch to eight features per inch.

The embodiments of the described methods and sampling bags are not limited to the particular embodiments, method steps, and materials disclosed herein as such formulations, process steps, and materials may vary somewhat. Moreover, the terminology employed herein is used for the purpose of describing exemplary embodiments only and the terminology is not intended to be limiting since the scope of the various embodiments of the present invention will be limited only by the appended claims and equivalents thereof.

Therefore, while embodiments of the invention are described with reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

The invention claimed is:

1. A sampling bag, comprising:
a top multilayer wall, wherein the top multilayer wall comprises:
   a top inner layer comprising a bottom surface, a top patterned periphery, wherein the top patterned periphery comprises a plurality of first teeth; and
   a top sealing layer;
a bottom multilayer wall, wherein the bottom multilayer wall comprises:
   a bottom inner layer comprising a top surface, a bottom patterned periphery, wherein the bottom patterned periphery comprises a plurality of second teeth, and the first teeth are not interlocked with the second teeth; and
   a bottom sealing layer;
wherein the top sealing layer is sealed to the bottom sealing layer to form a seam and the first teeth and the second teeth extend into the seam, the seam is sealed between the teeth, and the top inner layer and the bottom inner layer are in a face to face relationship with the bottom surface facing the top surface.

2. The sampling bag of claim 1, wherein the patterned periphery comprises a plurality of elements selected from a tab, a tongue, a tooth, a dog tooth, an aperture, a dovetail shape, jagged edge, rectangle, square, a scalloped pattern, or combinations thereof and a patterned periphery covering the entire perimeter of the inner layer.

3. The sampling bag of claim 1, wherein each of the top and bottom inner layers comprises an inner surface of stainless steel and each of the top and bottom sealing layers comprises a thermoplastic.

4. The sampling bag of claim 1, wherein each of the top and bottom inner layers comprises an inner surface of poly ether-ether-ketone and each of the top and bottom sealing layers comprises a thermoplastic.

5. The sampling bag of claim 1, wherein each of the top and bottom sealing layers comprises an inner surface comprising a thermoplastic.

6. The sampling bag of claim 1, wherein each of the top and bottom inner layers comprises an inner surface of polyvinylidene fluoride and each of the top and bottom sealing layers comprises a thermoplastic.

7. The sampling bag of claim 1, wherein each of the top and bottom sealing layers comprises thermoplastic and the thermoplastic is fused together to form a seal around the periphery of the sampling bag and between the teeth of the first and second inner layers.

8. The sampling bag of claim 7, wherein a portion of the patterned periphery of each of the top and bottom extends into the seam portion and the thermoplastic is fused together in an area between the teeth of the top and bottom inner layers.

9. The sampling bag of claim 8, wherein the portion of the patterned periphery is mechanically locked in the seam portion by the sealing layer.

10. The sampling bag of claim 6, wherein the top and bottom inner layers are attached together by an adhesive or a weld.

11. The sampling bag of claim 1, wherein the top and bottom multilayer walls comprise has an outer layer of comprising one of polyester, polyamide, polyimide, or a-combinations thereof; a thin aluminum layer; the sealing layer; and the inner layer for contacting the sample.

12. A sampling bag, comprising:
a first sealing layer comprising a thermoplastic and a second sealing layer comprising a thermoplastic, the two sealing layers sealed together by fusing the thermoplastic of the first sealing layer and the thermoplastic of the second sealing layer to form a fused thermoplastic seamed periphery portion; and
a first inner layer and a second inner layer each comprising a patterned periphery having teeth that extends into without protruding through the seamed periphery portion, wherein the first inner layer and the second inner layer consist essentially of a stainless steel, the first inner layer and the second inner layer are face to face, and the thermoplastic of the first sealing layer and the thermoplastic of the second sealing layer are fused between the teeth.

13. The sampling bag of claim 12, wherein the first sealing layer and second sealing layers comprise an inner surface comprising the thermoplastic.

14. The sampling bag, of claim 13, wherein the thermoplastic is one of polyethylene, polypropylene, copolymers of polyethylene and/or polypropylene, or a combination thereof.

15. The sampling bag of claim 12, wherein the patterned periphery comprises a plurality of elements selected from a tab, a tongue, a tooth, a dog tooth, an aperture, a dovetail shape, jagged edge, rectangle, square, a scalloped pattern, or combinations thereof.

16. The sampling bag of claim 15, wherein the pattern periphery is mechanically locked within the seamed periphery portion by the fused thermoplastic layer between teeth of the patterned periphery.

17. The sampling bag of claim 12, wherein the stainless steel is selected from one of is selected from a group comprising SST 304, SST 304L, 309, SST 309L, SST 316, SST 316L, SST 321, SST 321L and low carbon stainless steel.

18. The sampling bag of claim 12, wherein the inner layer has a thickness in a range from 10 microns to 100 microns.

19. The sampling bag of claim 12, wherein the outer layer comprises multiple layers of different materials and the inner most layer of the outer layer is one of polyethylene or polypropylene.

20. A sampling bag, comprising:
a first sealing layer comprising a thermoplastic and a second sealing layer comprising a thermoplastic, the two sealing layers sealed together by fusing the thermoplastic of the first sealing layer and the thermoplastic of the second sealing layer to form a fused thermoplastic seamed periphery portion; and
a first inner layer and a second inner layer each comprising a patterned periphery having teeth that extends into without protruding through the seamed periphery portion, wherein the first and second inner layers consist essentially of poly ether-ether-ketone, wherein the first inner layer and second inner layer are face to face and the thermoplastic of the first sealing layer and the thermoplastic of the second sealing layer are fused between the teeth.

21. The sampling bag of claim 12, wherein the patterned periphery of the first inner layer and second inner layer are aligned.

22. The sampling bag of claim 21, wherein the first inner layer and the second inner layer are connected together at the patterned periphery by a weld or adhesive.

* * * * *